US006852190B2

(12) United States Patent
Widlund (10) Patent No.: US 6,852,190 B2
(45) Date of Patent: Feb. 8, 2005

(54) METHOD FOR PRODUCING AN ABSORBENT ARTICLE

(75) Inventor: Urban Widlund, Pixbo (SE)

(73) Assignee: SCA Hygiene Products, Gothenburg (SE)

( * ) Notice: Subject to any disclaimer, the term of this patent is extended or adjusted under 35 U.S.C. 154(b) by 0 days.

(21) Appl. No.: 10/417,227

(22) Filed: Apr. 17, 2003

(65) Prior Publication Data

US 2003/0217447 A1 Nov. 27, 2003

Related U.S. Application Data

(60) Provisional application No. 60/373,338, filed on Apr. 18, 2002.

(51) Int. Cl.[7] ............................................. B32B 31/00

(52) U.S. Cl. ...................... 156/270; 156/161; 156/252; 156/253; 156/263; 156/251; 156/292; 156/265; 156/227; 156/300; 156/301; 156/302; 156/204

(58) Field of Search ................................. 156/300, 204, 156/227, 161, 252, 253, 263, 265, 269, 270, 251, 292, 299, 0, 301, 302, 303

(56) References Cited

U.S. PATENT DOCUMENTS

| 5,985,081 A | 11/1999 | Reynolds | ..................... 156/269 |
| 2001/0014798 A1 | 8/2001 | Femfors | ..................... 604/391 |

FOREIGN PATENT DOCUMENTS

| EP | 0 797 970 A2 | 10/1997 |
| EP | 1 108 372 A1 | 6/2001 |
| JP | 2000237233 A | 9/2000 |
| WO | WO 02/32360 A2 | 4/2002 |

Primary Examiner—Linda Gray
(74) Attorney, Agent, or Firm—Burns, Doane, Swecker & Mathis, L.L.P.

(57) ABSTRACT

A process for manufacturing an absorbent article includes continuously feeding a first web (1) along a travelling path, said first web(1) including a first and a second opposing strip (9, 10) extending in the longitudinal direction and a first panel portion (11) located therebetween, continuously feeding a second web (2) along a travelling path, said second web (2) including a third and a fourth opposing strip (25, 26) and a second panel portion (20) located therebetween, cutting the first panel portion (11) into a number of first panels (14, 15), cutting the second panel portion (20) into a number of second panels (25, 26), forming a joint web (3) by placing the second web (2) over the first web (1), cutting the joint web (3) along attachment lines thereby forming the absorbent articles (4).

12 Claims, 6 Drawing Sheets

METHOD FOR PRODUCING AN ABSORBENT ARTICLE

CROSS-REFERENCE TO RELATED APPLICATIONS

The present application claims the benefit of U.S. Provisional Application No. 60/373,338, filed in the United States on Apr. 18, 2002, the entire contents of which are hereby incorporated herein by reference.

BACKGROUND OF THE INVENTION

1. Technical Field

The invention relates to a process for manufacturing absorbent articles such as disposable pant diapers or diapers. The invention also relates to a product manufactured by the process. The process comprises the steps of continuously feeding a first web along a travelling path. The first web has a longitudinal direction coinciding with said travelling path and a transverse direction perpendicular to said longitudinal direction. The first web comprises a first and a second opposing strip extending in the longitudinal direction with a first panel portion therebetween. The process also comprises the steps of continuously feeding a second web along a travelling path. The second web has a longitudinal direction coinciding with said travelling path and a transverse direction perpendicular to said longitudinal direction. The second web comprises a third and a fourth opposing strip with a second panel portion therebetween.

2. Background Art

It has long been known to produce absorbent articles such as disposable pant diapers and diapers in an automated process plant. It is important to have speed in the process because the more absorbent articles that are produced per time unit, the shorter the time period necessary to achieve the desired number of produced absorbent articles. Due to the demands from customers, the quality of the produced articles is of course highly important. Moreover, a high production quality reflects upon the economy of the process, since it results in a low number of deficient absorbent articles which have to be discarded, thus keeping the waste to a minimum. Another important reason for minimizing the waste is that the manufacturer normally has to pay a fee for waste management, i.e., waste disposal. Furthermore, the waste involves a direct cost as a result of the loss of material.

A number of process methods have been proposed in order to meet the above mentioned demands. The most common way to reduce waste has been to manufacture the absorbent article in separate parts and to assemble the parts in a marriage point in the production line. However, a problem with this method is that the production is slow. In addition, there is an evident risk of assembling the parts incorrectly, resulting in deficient products and an increase in the production waste.

In order to overcome the problems associated with the production of absorbent articles from separately formed parts, a number of ways have been suggested. EP 0797970, for example, shows a process for manufacturing a sheet member forming a part of a disposable garment. A web intended to be used as a topsheet or a backsheet in a disposable garment and defining a front and a back section and a crotch section extending therebetween is continuously fed in its longitudinal direction. The web is divided in two halves along a longitudinally extending cutting line describing a wave-shaped curve approximate to a sine curve. In this manner, two webs are obtained. These two webs are moved in their transverse direction, resulting in a predetermined spacing between the webs. Moreover, one of the two webs is longitudinally shifted relatively to the other by a half period causing the webs to overlap at repeated intervals. Thereafter, the two webs are joined together in their overlapping regions. Thus, the two webs form a recombined web which is cut at intervals corresponding to the length of a wave period with a pair of overlapping regions arranged in the middle of each such wave period. In this manner, a topsheet or a backsheet can be manufactured without any waste pieces having to be cut therefrom.

Even though this process does not leave any waste, there are still some problems connected with the process. For example, the longitudinal shifting of one of the two webs slows down the manufacturing process. Further, both halves of the web are formed from the same material. Thus, in order to produce an absorbent article having special features such as different elasticity in different parts of the article (in order to conform better to the body of a user) additional components such as elastic material have to be applied to the web, either before or after the assembling of the two webs. Furthermore, since the web is divided in two halves along a longitudinally extending cutting line, it is necessary to provide special means in the process in order to keep the two halves in a similarly stretched state as before the division. If no stretching means are present, the two web halves may wrinkle or become distorted in some other way before the web halves are shifted and rejoined, which of course may result in a defective final product.

Thus, there still exists a need for an improved manufacturing process for absorbent articles. An objective of the invention is to provide a better and cheaper product, by offering a production line with a high volume of production and a high degree of productive power and with as little waste as possible.

SUMMARY

One embodiment of the invention includes a process for manufacturing an absorbent article, for example disposable pant diapers and diapers. The absorbent article comprises a front portion, a back portion, and a central portion extending therebetween. The absorbent article also comprises side portions, which side portions extend between the front portion and the back portion, and are intended to be fitted over the sides/hips of a user when in use. The central portion is intended to be fitted in the crotch region of a user.

One embodiment of an absorbent article according to the invention, comprises a liquid-impervious back sheet facing away from a user during use, and a liquid-pervious top sheet facing the user during use, and one or more absorbent bodies arranged therebetween.

The back sheet may be of any liquid-impermeable material or of a material that has been made liquid-impermeable. Examples of suitable materials are plastic films, treated nonwoven materials and laminates of nonwoven or nonwoven and plastic film.

The top sheet may be of any inherently liquid-permeable material or of a material that has been treated to be liquid-permeable. Examples of such materials are, nonwoven, textiles, netting or perforated plastic film.

The absorbent bodies may be of any liquid-retaining material, or layers of liquid-retaining material, or a combination of liquid-distributing material and liquid-retaining material. The absorbent body may also comprise a superabsorbent material. A superabsorbent material is an absorbent polymer material capable of absorbing fluids in an amount corresponding to several times the dry weight of the superabsorbent material and which upon absorption swells into a fluid-containing gel.

The process according to one embodiment of the invention for manufacturing an absorbent article includes the steps of:

a) continuously feeding a first web along a travelling path, said first web having a longitudinal direction coinciding with said travelling path and a transverse direction perpendicular to said longitudinal direction, said first web comprising a first and a second opposing strip extending in the longitudinal direction and a first panel portion located therebetween; and
b) continuously feeding a second web along a travelling path, said second web having a longitudinal direction coinciding with said travelling path and a transverse direction perpendicular to said longitudinal direction, said second web comprising a third and a fourth opposing strip and a second panel portion located therebetween.

The process may comprise the further steps of:

c) cutting the first panel portion along generally transversely extending first and second cutting lines into a number of first panels, which first panels are attached to the first and second strips. The cutting of the first panel portion may be done in such a way that the first panel portion is separated into a number of first front panels comprising a first forward part attached to the second strip and an opposing first central part attached to the first strip, and a number of first back panels comprising a first rear part attached to the first strip and an opposing second central part attached to the second strip. The first front and back panels may advantageously be cut in such a way that they appear in an alternating (every second) pattern on the first web. Furthermore, the cutting may be done in such a way that the first front and back panels are aligned in said longitudinal direction of said first web with every first front panel being rotated 180° with respect to first back panel.
d) cutting the second panel portion along generally transversely extending third and fourth cutting lines into a number of second panels, which second panels are attached to the third and fourth strips. The cutting of the second panel portion may be done in such a way that the second panel portion is separated into a number of second front panels comprising a second forward part attached to the fourth strip and an opposing third central part attached to the third strip, and a number of second back panels comprising a second rear part attached to the third strip and an opposing fourth central part attached to the fourth strip. The second front and back panels may advantageously be cut in such a way that they appear in an alternating pattern on the second web. Furthermore, the cutting may be done in such a way that the second front and back panels are aligned in said longitudinal direction of said second web with every second front panel being rotated 180° with respect to every second back panel.
e) forming a joint web by placing the second web over the first web and attaching the first web to the second web with seams along attachment lines such that the panels and the strips along the seams divide the joint web into a number of absorbent articles. The seams are placed such that they appear in the central portion of the absorbent article, and there may also be seams that appear on the side portions of the absorbent article. One way to form the joint web is to feed one of the first or second webs into the process upside down and then place it over the other web. Another way to form the joint web is to fold one of the first or second webs over the other.
f) cutting the joint web along the attachment lines thereby forming the absorbent articles.

The first web, second web and the joint web are stretched out in their transversal direction, i.e. the direction perpendicular to the travelling direction, during the process and when the first and second panel portions are cut, the panels are still attached to the strips. The panels are thus also stretched out in their transversal direction, thereby enabling a number of cutting possibilities of the panel portions in order to gain different features of the final product. Since the webs are stretched out during the process, there is no need for a special holding device for holding the panel portion and keeping it from deforming. The stretching of the different parts of the web is sufficient, which of course is a big advantage compared to prior art where such special holding arrangements are necessary during the manufacturing process in order to prevent different parts of the absorbent article from deforming.

The joint web may advantageously be formed by bringing together the first web and the second web such that the first front panels are placed against the second back panels with the first central parts against the fourth central parts, and the second front panels are placed against the first back panels with the second central parts against the third central parts.

In one embodiment of the invention, the attachment of the first web to the second web is done by attaching each of the second central parts to each of the third central parts by a first seam along a first attachment line, and attaching each of the first central parts to each of the fourth central parts by a second seam along a second attachment line, thereby forming the central portions of the absorbent articles. The first and second seams are advantageously of a permanent type, but may be of a reclosable type.

In the final product, i.e. the absorbent article, the first and second seams will appear in the central portion of the article.

Thereafter, the joint web may be cut, in a final cutting step, in such a way that parts of the first and fourth strips together with the first back panel and the second front panel form a first absorbent article separated from the joint web, and that parts of the second and third strips together with the second back panel and the first front panel form a second absorbent article separated from the joint web.

The process may further comprise the steps of;

attaching the first strip to the fourth strip by third seams, preferably along the first- and second parallel attachment lines, and
attaching the second strip to the third strip by fourth seams, preferably along the third and fourth parallel attachment lines.

In the final product, i.e. the absorbent article, the third and fourth seams will appear in the waist side portions of the article, attaching the front portion to the back portion. The length of the strips, i.e. front and back waist portions of the article, decides where on the waist side portions of the article the third and fourth seams will appear during use. For example, if the strips are of equal length the third and fourth seams will appear centrally on the side portion, and if the strips have different lengths the third and fourth seams may be displaced towards either the front portion or the back portion of the article.

The attachment of the strips may be done either after the final cutting or before the final cutting, where the final cutting will be done according to the steps of;

the joint web being cut along fifth cutting lines between the third seams, preferably between the first and second parallel attachment lines, and along the first attachment line, and the joint web being cut along sixth cutting lines between the fourth seams, preferably between the third and fourth parallel attachment lines, and along the second attachment line.

The joint web is advantageously cut along the fifth cutting line and sixth cutting line such that the first, second, third, fourth, fifth and sixth cutting lines coincide at least partly.

The first, second, third, and fourth seams may be of a reclosable kind, for example a hook and loop material, or a reclosable tape material, or any other suitable reclosable material. The seams may also be of a permanent kind, for example formed by gluing, heat bonding, or ultrasonic welding, or by any other suitable sealing or bonding operation.

As described above, the cutting of the first and second webs generates a number of first front and back panels and a number of second front and back panels. Each of the first, second, third, and fourth cutting lines have been described as being one single transversely extending cutting line extending from one strip to another over the panel portion, but each of the cutting lines may be formed by a number of cutting lines coinciding at least partly.

The feature of each cutting line decides the shape of the front and back panels. For example, the first and second cutting lines may be cut as straight lines perpendicular to the first and second strip generating a first front panel that is similar to the first back panel, such that they appear in an alternating pattern on the first web. The first and second cutting lines may also be cut as straight lines at an angle to the first and second strip generating a triangular shaped first front panel similar to a triangular shaped first back panel, such that they appear in an alternating pattern on the first web but rotated 180° with respect to each other.

To explain further the role of the cutting lines, each cutting line can be described as delimiting the sides of both a front panel and a back panel. For example, the first and second cutting lines are repeated in an alternating way on the first web. The first cutting line divides the panel portion in such a way as to shape one side of the first front panel in one way and the adjacent side of the first back portion in a corresponding way. The second cutting line divides the panel portion in such a way as to shape another side of the first front panel in another way and the adjacent side of the first back portion in a corresponding way. The repetition of the alternating first and second cuts generates first front and back portions that correspond to each other depending on the features of the cutting lines. The third and fourth cutting lines have the same role for the second web.

In one embodiment of the invention, the first web may be cut in such a way that each first and second front panel obtains a two-dimensional funnel shape, and each first and second back panels obtain a two-dimensional cup shape, but any other suitable shape of the front and back panels is feasible.

However, the cutting of the panel portion of the web does not have to be made only along a cutting line, but may involve a part of the panel portion being cut out from the web. The cut-out panel portion may be in any shape suitable for the purpose of forming a product with a desired configuration or shape. For example, the cut away part may have an oval shape, round shape, rectangular shape etc.

As mentioned before, the first web and the second web are both stretched in the transverse direction (i.e. the direction perpendicular to the feeding direction of the web) during the whole process. Since the panel portions are attached to the strips during the entire process, each panel portion may be cut in any suitable pattern, without the various first panels and second panels ending up with free ends that may deform or that need special attachment devices.

The strips according to embodiments of the invention form a waist part of the absorbent article, which waist part comprises a front waist part, a back waist part and two side waist parts therebetween. The back waist part together with a part of the back panel (the rear part) forms the back portion of the absorbent article. The front waist part together with a part of the front panel (forward part) forms the front portion of the absorbent article. The central part of the front panel together with the central part of the back panel forms the central portion of the absorbent article. The two side waist parts each form the side portions in the absorbent article, which side portions extend between the front portion and the back portion, and are intended to be fitted over the sides/hips of a user when in use.

It is common to add different kinds of elastic means to the absorbent article in order to obtain a desired shape, for example leg elastics, standing gathers, waist elastics and other suitable shaping arrangements.

Thus, the process may further comprise the step of applying elastic means to the first web and/or on the second web.

The elastic means may be applied to the web using any known technique, for example by continuously and directly attaching elastic means on the continuously fed web, or by arranging the elastic means on a template carrying guiding pins for the elastic means.

The waist parts may have different elastic features, and may, for example, be all elastic or only partly elastic. The waist parts may be made all elastic by using an elastic fabric for the strips or by applying a number of elastic threads to the strips. Alternatively, the waist parts may be made partly elastic for example by adding elastic means to the strips only on selected portions of the web with predetermined distances between the elastic means. The waist parts may also be equipped with elastic means in such a way that the front portion and/or the back portion become elastic. It is also possible to apply elastic means, for example standing gathers, to the web in the panel portion in order to form side leakage barriers.

The panel portions may thus be of any material suitable for the purpose, for example non-elastic or elastic, as desired. Furthermore, the panel portion may contain one or several layers being liquid-impervious. Such a liquid-impervious layer may be arranged over all or only a part of the panel portion.

When making absorbent articles such as pant diapers or the like, it is of course advantageous to provide the articles with an absorbent body.

The process may therefore further comprise the step of placing first absorbent bodies along the first web with a predetermined distance between the absorbent bodies.

The first absorbent bodies are then advantageously applied to the first web in a double folded manner on the front and back panels, so that when the second web is placed over the first web, the double folded absorbent bodies will be applied over the corresponding front and back panels on the second web. Subsequently, when the final product is cut from the joint web (after the final cut), the first absorbent body will cover the front portion, the central portion and the back portion of the absorbent article.

Another way to add absorbent bodies to the process is to; apply the first absorbent bodies to the first web in a non-folded manner, with half the double folded length, and to; apply the second absorbent bodies to the second web with a predetermined distance between the absorbent bodies, which second absorbent bodies are applied to the second web in a non-folded manner.

The first and second absorbent bodies may overlap each other in the final absorbent article, or the first and second absorbent bodies may lie adjacent to each other in the central portion. The first and second absorbent bodies may be attached to each other by gluing, heating, welding, needling, or by any other suitable bonding technique. The attachment of the first and second absorbent bodies may be done at the same time as the first and second seams are applied or on a different occasion. The first and second absorbent bodies are advantageously attached by permanent means, but may be attached with reclosable means.

In another embodiment of the invention, the absorbent bodies are in the form of absorbent inserts, i.e., a unit that can be permanently or removably applied to that side of the absorbent article that faces the user during use. Such an absorbent unit may comprise a liquid-impervious layer, a liquid-pervious layer and one or more absorbent layers therebetween. The absorbent unit may also be equipped with any type of conventional liquid-retaining devices, such as standing gathers, side barriers, leg elastics, humps, and superabsorbent materials.

Depending on the features of the absorbent unit, the absorbent article, i.e., the web, may be of any suitable material. For example, if the absorbent unit has a liquid-impervious layer and a liquid-retaining system, the web making up the absorbent article may partly or totally be of a suitable breathable material, and if the absorbent unit lacks a liquid-impervious layer, the web may partly or totally be of any suitable liquid-impermeable material.

The absorbent units may be placed on the web or between layers of the web at any time during the process, or may even be placed in the final absorbent article.

The absorbent unit may be equipped with fastening means on that side of the liquid-impervious layer that lies adjacent the absorbent article, in order to keep the absorbent unit in place in the absorbent article.

The invention also refers to a product manufactured by the process.

BRIEF DESCRIPTION OF DRAWINGS

The present invention will become more fully understood from the detailed description given hereinbelow and the accompanying drawings wherein.

DETAILED DESCRIPTION OF THE PREFERRED EMBODIMENTS

The production process for manufacturing an absorbent article according to the invention will be shown in a number of embodiments, which embodiments shall not be seen as limiting for the invention, but merely as examples of different ways to use the process. In the text some embodiments have been denoted as, for example, "embodiment A)" or "embodiment B)". However, this does not indicate a first or second embodiment, but is merely a denotation in order to facilitate the understanding of the description of the different embodiments.

Figure 1:
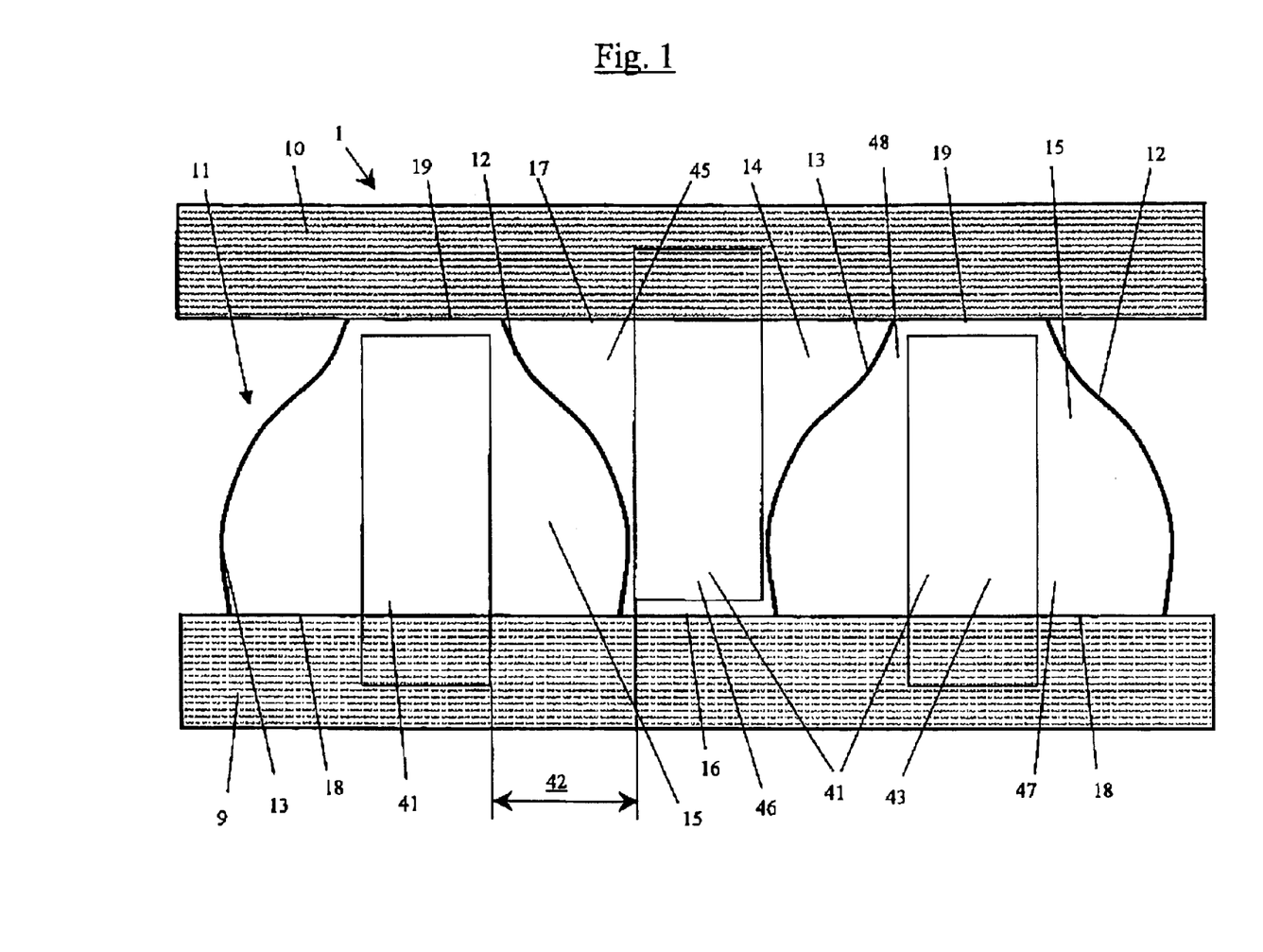
FIG. 1 shows a first web on a production line according to an embodiment of the invention.
Figure 2:
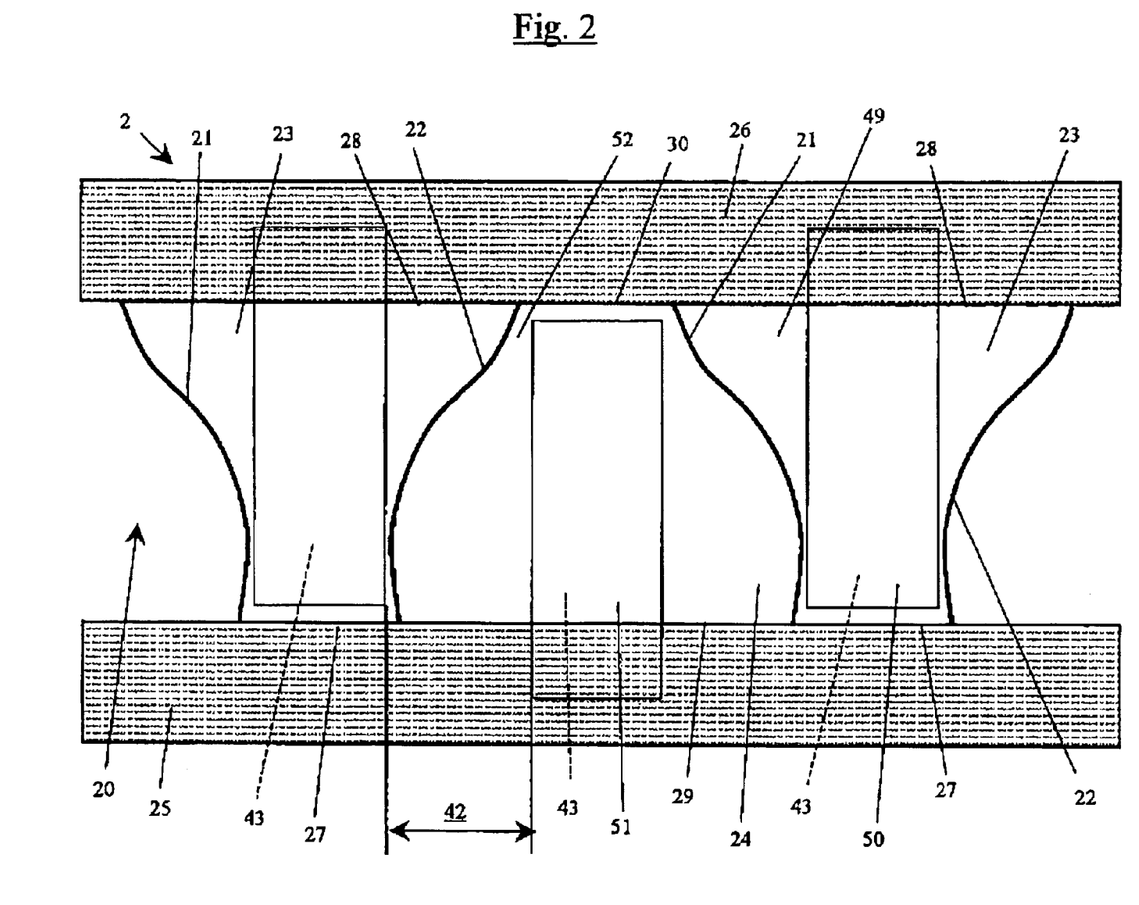
FIG. 2 shows a second web on a production line according to an embodiment of the invention.
Figure 3:
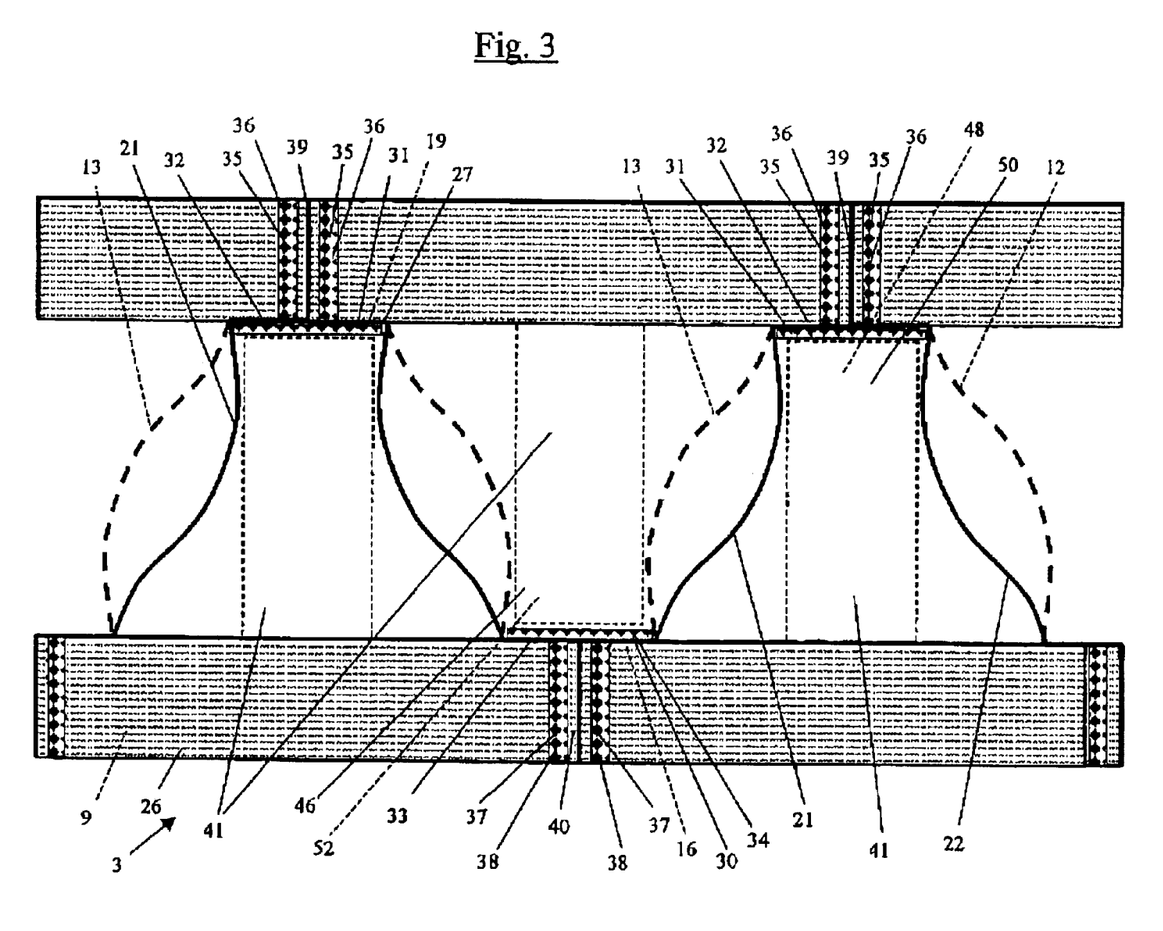
FIG. 3 shows a joint web formed by the first web and the second web on a production line according to an embodiment of the invention.

FIG. 1 shows a first web 1, FIG. 2 shows a second web 2 and FIG. 3 shows a joint web 3 comprising the first 1 and second 2 webs according to the invention. The different webs form parts of a production line according to the invention, in a process for manufacturing an absorbent article 4, for example a disposable pant diaper or other type of diaper.

The process is intended for manufacturing an absorbent article 4 comprising a front portion 5, a back portion 6 and a central portion 7 extending therebetween, which central portion extends in the crotch area of a user during use. The absorbent article also comprises two side portions 8 extending between the front portion 5 and the back portion 6 over the waist sides of a user when in use.

The process for manufacturing the absorbent article 4 according to one embodiment of the invention includes the steps of a)–h.) below:

a) continuously feeding a first web 1 comprising a first 9 and a second 10 opposing strip, with a first panel portion 11 therebetween in a transverse direction thereof.

b) transversely cutting the first panel portion 11 of the first web 1 along a first cutting line 12 and along a second cutting line 13, dividing the first web into a number of first front panels 14 and a number of first back panels 15. The cutting lines extend from the first strip 9 to the second strip 10. The first front panels 14 each comprise a first end edge 16 between the first and second cutting lines 12, 13 along the first strip 9, and a second end edge 17 between the first and second cutting lines 12, 13 along the second strip 10. The first back panels 15 each comprise a third end edge 18 between the first and second cutting lines 12, 13 along the first strip 9, and a fourth end edge 19 between the first and second cutting lines 12, 13 along the second strip 10. The first and second cutting lines 12, 13 may be mirror images of each other.

c) continuously feeding a second web 2 comprising a third 25 and a fourth 26 opposing strip with a second panel portion 20 therebetween in a transverse direction thereof.

d) transversely cutting the second panel portion 20 of the second web 2 along a third cutting line 21 and along a fourth cutting line 22, separating the second web into a number of second front panels 23 and a number of second back panels 24. The cutting lines extend from the third strip to the fourth strip. The second front panels 23 each comprise a fifth end edge 27 between the third and fourth cutting lines 21, 22 along the third strip 25, and a sixth end edge 28 between the third and fourth cutting lines 21, 22 along the fourth strip 26. In a corresponding manner, the second back panels 24 each comprise a seventh end edge 29 between the third and fourth cutting lines 21, 22 along the third strip 25, and an eighth end edge 30 between the first and second cutting lines 21, 22 along the fourth strip 26. The third and fourth cutting lines 21, 22 may be mirror images of each other.

e) continuously feeding a joint web 3 comprising the second web 2 placed over the first web 1 in such a way that the third strip 25 is placed over the second strip 10, and the fourth strip 26 is placed over the first strip 9, with the fourth end edge 19 adjacent the fifth end edge 27 and the eighth end edge 30 adjacent the first end edge 16.

f) attaching the first web 1 to the second web 2 by a first seam 31 along first attachment lines 32 essentially, or at least partly, coinciding with (or essentially parallel to) the second and third strips 10, 25 and essentially, or at least partly, coinciding with (or essentially parallel to) the fourth and fifth end edges 19, 27. The first attachment lines 32 are preferably placed between the first, second, third and fourth cutting lines 12, 13, 21, 22 parallel to or coinciding with the fourth and fifth end edges 19, 27. The first web 1 is also attached to the second web 2 by a second seam 33 along second attachment lines 34 essentially, or at least partly, coinciding with (or essentially parallel to) the first and fourth strips 9, 26 and the first and eighth end edges 16, 30. The second attachment lines 34 are preferably placed between the first, second, third and fourth cutting lines 12, 13, 21, 22 parallel to or coinciding with the first and eighth end edges 16, 30. The first web 1 is also attached to the second web 2 by third seams 35 along first and second parallel attachment lines 36 essentially perpendicular to the first attachment lines 32, and by fourth seams 37 along third and fourth parallel attachment lines 38 essentially perpendicular to the second attachment lines 34. However, the parallel attachment lines 36, 38 as well as the third and fourth seams 35, 37 may be at an angle to the first and second attachment lines 32, 34 respectively. Each of the third seams 35 and the fourth seams 37 advantageously comprises two parallel seams.

The third seams 35 advantageously bond the third strip 25 to the second strip 10, and the fourth seams 37 advantageously bond the fourth strip 26 to the first strip 9. The third seams 35 are advantageously placed in close vicinity to the first seam 31 between the end points of the first seam 31. The fourth seams 37 are advantageously placed in close vicinity to the second seam 33 between the end points of the second seam 33.

The attachment of the first web 1 to the second web 2 at the seams 31, 33, 35, 37 can be performed by any known bonding method. Suitable methods involve adhesive bonding, heat bonding, ultrasonic welding, needling, hydroentangling, etc. If desired, the seams can be made breakable by selecting a bonding strength which will withstand wearing conditions but which will allow the seams to be torn open manually. The attachment may also be done in such a way that the absorbent article 4 becomes reclosable, for example by using hook and loop materials.

The attachments according to the above give a stretched out absorbent article 4, where parts of the strips 9, 10, 25, 26 together with a part of each front panel 14, 23 become the front portion 5, and where parts of the strips 9, 10, 25, 26 together with a part of each back panel 15, 24 become the back portion 6, and where parts of the panel portions 5, 6 form the central portion 7 of the absorbent article.

g) cutting the joint web 3 along an essentially T-shaped fifth cutting line 39 placed between the first and second parallel attachment lines 36 and along the first attachment line 32, and cutting the joint web 3 along an essentially T-shaped sixth cutting line 40 placed between the third and fourth parallel attachment lines 38 and along the second attachment line 34.

The transversal extending bar in the T-shaped cutting lines 39, 40 coincides with at least the first, second, third and fourth cutting lines. The T-shaped cutting lines 39, 40 may of course be cut in different ways, for example by a T-shaped cutting tool, or an L-shaped cutting tool and a straight cutting tool, or two perpendicular straight cutting tools.

The T-shaped cutting lines may also have another shape than being in the form of two straight lines. They may, for example, have somewhat skew parts, and/or somewhat curve-shaped parts.

h) separating the joint web 3 along the cutting lines 12, 13, 21, 22, 39, 40, thereby forming the absorbent article 4.

The joint web 3 is advantageously cut along the fifth cutting line 39 between the third seams 35 and along the first attachment lines 32, and the joint web 3 is also cut along a sixth cutting line 40 between the fourth seams 37 and along the second attachment lines 34, such that the first, second, third, fourth, fifth and sixth cutting lines coincide at least partly.

As is shown in FIGS. 1–3, the first and second cutting lines 12, 13 cut the first web 1 in such a way that each first front panel 14 obtains a planar funnel shape, and each first back panel 15 obtains a planar cup shape, and that the third and fourth cutting lines 21, 22 cut the second web 2 in such a way that each second front panel 23 obtains a planar funnel shape, and each second back panel 24 obtains a planar cup shape.

The first, second, third, and fourth cutting lines 12, 13, 21, 22 may of course be in any other shape dependent on the desired shape of the absorbent article. However, the shape of the back panels 15, 24 and front panels 14, 23 according to the embodiment shown in FIGS. 1–5 give an absorbent article 4 with a front portion 5 which is narrower than the back portion 6, and a somewhat hourglass-shaped central portion 7 extending therebetween.

However, the first, second, third, and fourth cutting lines 12, 13, 21, 22 may be straight lines, perpendicular to the strips, thereby forming a square pattern when the T-shaped cutting lines 39, 40 cut the joint web 3. The first, second, third, and fourth cutting lines 12, 13, 21, 22 may also be straight lines at an angle to the strips, thereby forming an absorbent article with hour-glass shape when the article is in an unfolded state. The first, second, third, and fourth cutting lines 12, 13, 21, 22 may, of course, have any selected curved shape across the panels between the strips 9, 10, 25, 26, thereby offering the possibility of forming absorbent articles with a number of different shapes.

In order to further describe the assembling of the absorbent article, the first front panels 14 may be described as each comprising a first forward part 45 attached to the second strip 10 and an opposing first central part 46 attached to the first strip 9. Correspondingly, the first back panels 15 may be described as comprising a first rear part 47 attached to the first strip 9 and an opposing second central part 48 attached to the second strip 10.

The second front panels 23 may in a similar way be described as comprising a second forward part 49 attached to the fourth strip 26 and an opposing third central part 50 attached to the third strip 25. Further, the second back panels 24 may be described as comprising a second rear part 51 attached to the third strip 25 and an opposing fourth central part 52 attached to the fourth strip 26.

As described above, the first web 1 and the second web 2 are brought together forming a continuously fed joint web 3 such that the first front panels 14 are placed against the second back panels 24 with the first central parts 46 against the fourth central parts 52, and the second front panels 23 are placed against the first back panels 15 with the second central parts 48 against the third central parts 50.

Thereafter, the second central parts 48 are attached to the third central parts 50 by the first seam 31 along the first attachment lines 32, and the first central parts 46 are attached to the fourth central parts 52 by the second seam 33 along the second attachment lines 34, thereby forming the central portions 7 of the absorbent articles 4.

It is also possible to add additional features in the process of manufacturing the absorbent article according to the above. When using the absorbent article as a disposable diaper it is of course advantageous to use at least one absorbent body in the absorbent article. The process described above in steps a.)–h.) may be used, for example, when manufacturing disposable diaper pants. In such a case, first absorbent bodies 41 are placed along the first web with a predetermined distance 42 between the absorbent bodies. The absorbent bodies may be in any suitable shape such as hourglass shaped or, as is shown in FIGS. 1 and 3, a rectangular shape.

According to step f) the first web 1 is attached to the second web 2 along the first attachment line 32 and along the second attachment line 34, which first and second attachment lines 32, 34 will be placed in the central portion 7, i.e. the crotch portion, of the absorbent article or disposable diaper pant.

Embodiment A):

It is especially advantageous to apply the first absorbent bodies 41 to the first web 1 in a double folded manner, with the bent over part towards the second strip 10. This is advantageous since when the first web 1 is attached to the second web 2 along the first attachment line 32 and along the second attachment line 34 according to step f), the double folded first absorbent bodies 41 do not take part in the attachment process. Since the first absorbent body 41 does not take part in any attachment process between a number of absorbent bodies, the first absorbent bodies will not be negatively affected by the attachment and will not display, for example, a weld bead, or any another disruption of the surface of the absorbent body. Thus, the first absorbent body 41 will exhibit a continuous layer in the crotch portion of a user when in use.

The first absorbent body 41 may be in the form of a double folded layer, placed between the first and second cutting lines 12, 13 on both the back panels 15, 24 and the front panels 14, 23 of the first web. The double folded first absorbent body/layer may then be attached to the first web 1 when applied to the first web 1. The first double folded body/layer may then additionally be attached either to the back panels 15, 24, and/or to the front panels 14, 23, and/or to the panel portions when the second web 2 is joined according to any of the steps e)–h).

Double folded absorbent bodies may also be placed on both the first web 1 and the second web 2. For example, the double folded first bodies 41 may be placed only on the first front panels 14 on the first web 1 and on the second front panels 23 on the second web 2. By placing the double folded first absorbent bodies 41 in such an alternating way, the first absorbent bodies will be covering all panels 14, 15, 23, 24 when the joint web 3 is formed. For the same reason, the double folded first absorbent bodies 41 may be placed only on the first back panels 15 on the first web 1 and on the second back panels 24 on the second web 2. The double folded absorbent bodies may also be placed on the first and second webs 1, 2 on all the panels 14, 15, 23, 24, enabling the possibility to have two absorbent bodies on the panels when the joint web 3 is formed.

The double folded absorbent bodies 41 may also have different features on different parts of the absorbent body. One part may have excellent liquid handling capability and another part may have excellent capability for handling faeces.

Embodiment B):

Another way to apply absorbent bodies when manufacturing disposable diaper pants, is to use the following steps:

first absorbent bodies 41 are applied to the first web at a predetermined distance 42 between the absorbent bodies. The first absorbent bodies 43 are preferably applied to the first web in one layer in a non-folded manner with each first absorbent body 41 preferably having half the length of the double folded first absorbent bodies 41 in embodiment A), and;

second absorbent bodies 43 are applied to the second web at a predetermined distance 42 between the absorbent bodies. The second absorbent bodies 43 are preferably applied to the second web in one layer in a non-folded manner with each second absorbent body 43 preferably having half the length of the double folded first absorbent bodies 41 in embodiment A).

One advantage with embodiment B) is that two different types of absorbent bodies can be applied to the webs 1, 2. For example, one absorbent body with excellent handling capacity for faeces and one for urine.

The absorbent bodies in embodiment B) may also be attached to the back panels 15, 24 and the front panels 14, 23 in different ways creating different properties for the front portion and the back portion of the absorbent article. The first and second absorbent bodies may be arranged in an overlapping manner or may be arranged edge to edge. When the first and second absorbent bodies are arranged in an overlapping manner, any of the first or second absorbent bodies may have a length longer than the other. The length of the first or second absorbent bodies may also exceed half the length of the absorbent bodies according to embodiment A).

Both embodiment A) and embodiment B) are shown in FIGS. 1–5. In FIG. 1, the first absorbent bodies 41 are shown as rectangular items. In embodiment A) the rectangular items represent the double folded first absorbent bodies 41, and in embodiment B) the rectangular items represent the non-folded second absorbent bodies 43.

One additional advantage of applying absorbent bodies to the web according to the invention (embodiment A) or B)) is that the absorbent bodies can be placed on any desired place within the absorbent diaper pant. It is only a question of where to place the absorbent body on the web 1, 2. The absorbent bodies 41, 43 may, for example, be placed in such a way that they are somewhat displaced towards the back portion 6 or they may be displaced in the opposite direction, i.e. towards the front portion 5.

Figure 4:
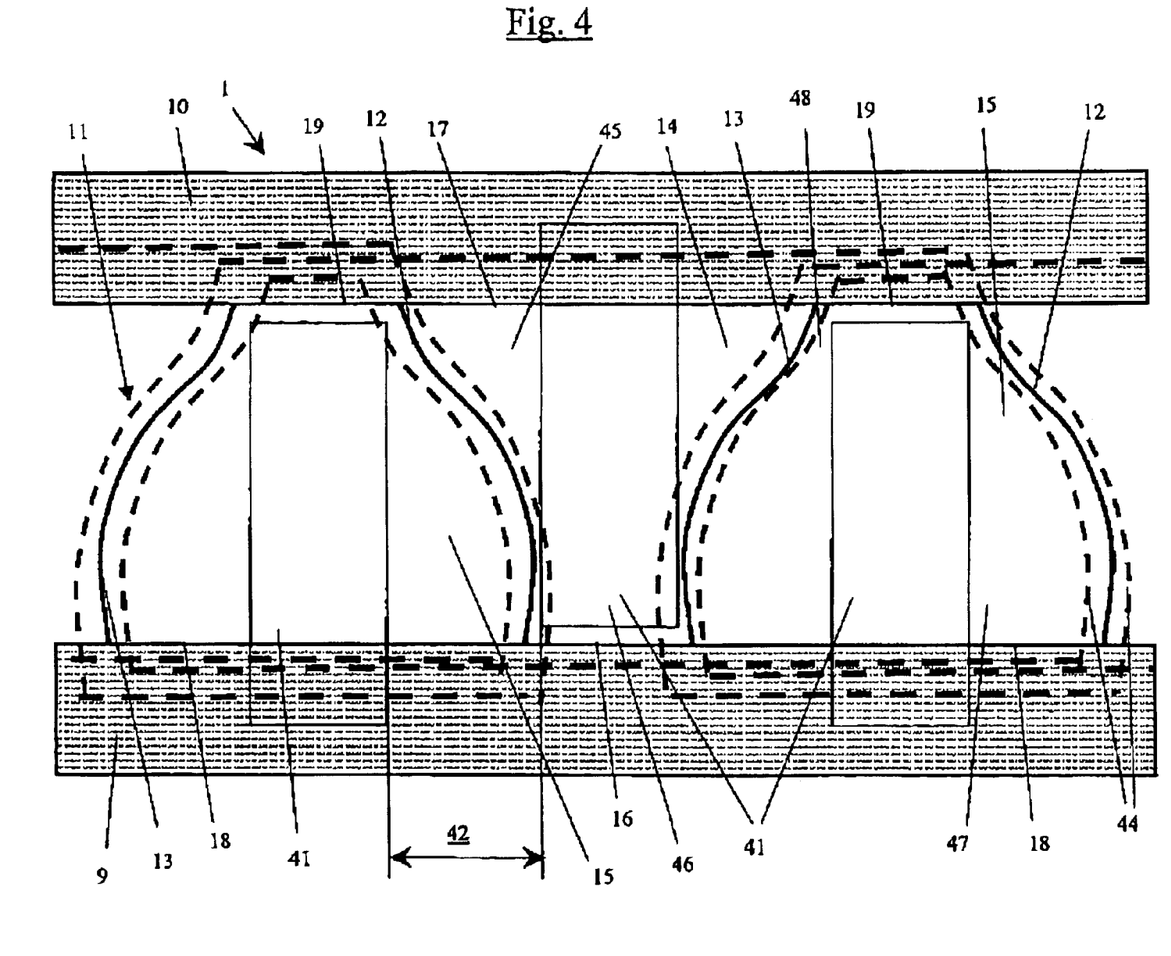
FIG. 4 shows the first web with elastic means applied according to an embodiment of the invention.
Figure 5:
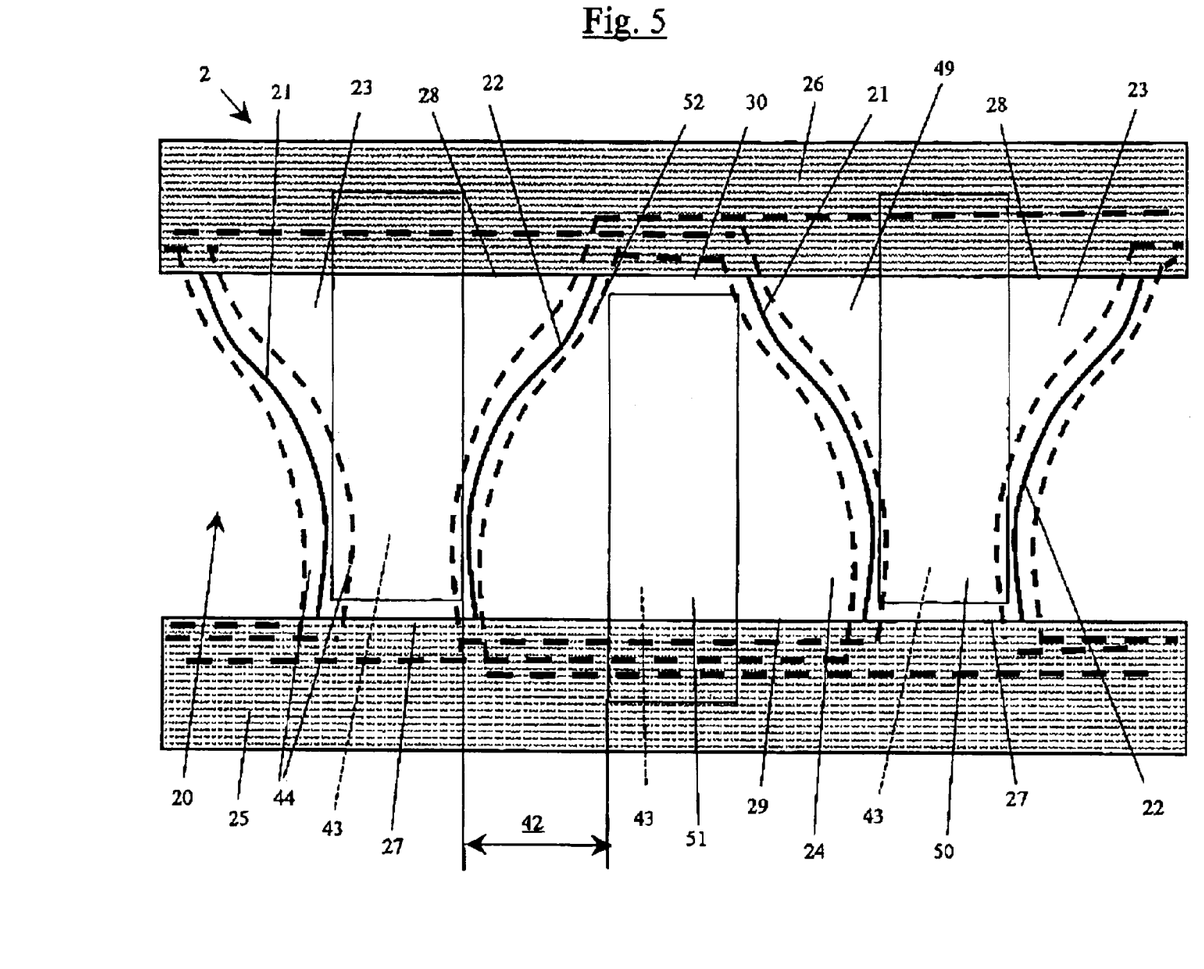
FIG. 5 shows the second web with elastic means applied according to an embodiment of the invention.
Figure 6:
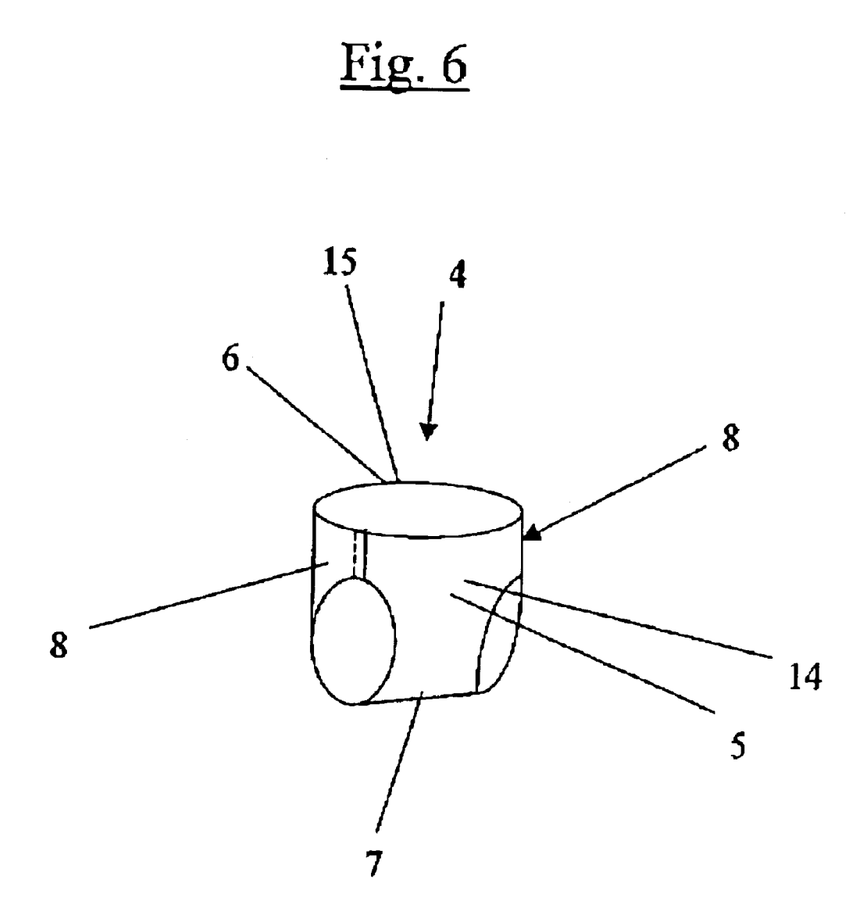
FIG. 6 shows an absorbent article manufactured by means of a process according to an embodiment of the invention.

Embodiment C):

In FIGS. 4 and 5 an additional embodiment is depicted, where elastic means 44 are placed on the first web 1 and on the second web 2.

According to FIGS. 4 and 5, a process for manufacturing an absorbent article according to one embodiment is characterised in that elastic means are applied in the following steps:

first elastic means 44 are continuously applied to the first web 1 in a pattern describing a generally straight line on and along the first strip 9, preferably at a distance from the third end edges 18, and on each of the first back panels 15 in a curve shape along an inside of the second cutting line 13 on and along the second strip 10, preferably at a distance from the fourth end edges 19, and along an inside of the first cutting line 12.

second elastic means 44 are continuously applied to the first web 1 in a pattern describing a generally straight line on and along the second strip 10, preferably at a distance from the second end edges 17, and on each of the first front panels 14 in a curve shape along an outside of the second cutting line 13 and in a somewhat straight line on and along the first strip 9, preferably at a distance from the first end edges 16, and in a curve shape along an outside of the first cutting line 12.

third elastic means 44 are continuously applied to the second web 2 in a pattern describing a generally straight line on and along the third strip 25, preferably at a distance from the seventh end edges 29, and on each of the second back panels 24 in a curve shape along an inside of the fourth cutting line 22 and on and along the fourth strip 26, preferably at a distance from the eighth end edges 30, and along an inside of the third cutting line 21.

fourth elastic means 44 are continuously applied to the second web 2 in a pattern describing a somewhat straight line on and along the fourth strip 26, preferably at a distance from the eighth end edges 30, and on each of the second front panels 23 in a curve shape along an outside of the fourth cutting line 22 and in a generally straight line on and along the third strip 25, preferably at a distance from the seventh end edges 29, and in a curve shape along an outside of the third cutting line 21.

In another embodiment (not shown), the elastic means 44 are applied to the first web and the second web at least on one side of each of the cutting lines 12, 13, 21, 22, for example in a zigzag pattern from one strip to another close to the cutting lines 12, 13, 21, 22.

In yet another embodiment, the elastic means 44 are applied to the first web and the second web along each side of each of the cutting lines 12, 13, 21, 22, for example in a zigzag pattern from one strip to another close to the cutting lines 12, 13, 21, 22.

It is especially advantageous to place the first elastic means 44 on the first strip 9 at a distance from the first end edges 16, at least in a section delimited by the third and fourth parallel attachment lines 38, and to place the second elastic means 44 on the second strip 10 at a distance from the fourth end edges 19, at least in a section delimited by the first and second parallel attachment lines 36, and to place the third elastic means 44 on the third strip 25 at a distance from the fifth end edges 27, at least in a section delimited by the first and second parallel attachment lines 36, and to place the fourth elastic means 44 on the fourth strip 26 at a distance from the eighth end edges 30, at least in a section delimited by the third and fourth parallel attachment lines 38.

If the elastic means 44 are placed at the above mentioned distances from said end edges 16, 17, 18, 19, 27, 28, 29, 30, the cutting tools cutting the T-shaped fifth and sixth cutting lines 39, 40 will also cut away the elastic means placed crossing the cutting lines and lying in the strip area.

Thus, this placing of the elastic means 44 enables the process to cut away the parts of the elastic means that otherwise would appear in the central portion of the absorbent article or disposable diaper pant. Most processes for manufacturing absorbent articles or the like, place elastic means in the central portion of the pant due to ease in the production logistics. It is well known that elastic means stretched in a transversal direction in the central portion of an absorbent article, may distort the pant in an undesired way, and may also cause discomfort for a user. For example, a user may feel the strips in the central portion, i.e. the crotch portion, through the absorbent body.

However, the different elastic means 44 may be placed on the webs 1, 2 in such a way that the elastic means are not cut away during the cutting process. For some embodiments, elastic means in the crotch portion may give rise to a better fit.

The elastic means 44 placed on the strips 9, 10, 25, 26 form waist elastics on the absorbent article and the elastic means placed along the cutting lines 12, 13, 21, 22 form leg elastics in the central portion 7 of the article and make the absorbent article fit snugly around the legs of a user. The elastic means along the cutting lines may also give rise to side protection means, such as standing gathers and the like.

The invention shall not be seen as being limited by the above mentioned embodiments, but may have various features within the scope of the invention. For example, a liquid-pervious cover layer may also be arranged on the side of the absorbent article 1, which is intended to face the user during use, covering the absorbent body.

The absorbent bodies may comprise different layers with the same or different features. For example, one layer may be of a liquid-retaining material and one layer may be of a material that distributes and transports liquid well.

The first and the second webs may preferably be of a liquid-impervious material, forming the part of the absorbent article or diaper that is intended to face away from a user during use, but may alternatively be liquid-impervious only in selected regions.

The strips may be of an all-elastic material, but may also comprise a sheet with elastic threads or strips, with suitable elasticity, applied in suitable places along the sheet. The sheet may be a fabric or a nonwoven or any other suitable material.

Since the process is a continuous process, it is advantageous to let the different webs run via different rollers equipped for different purposes. The cutting may for example be carried out by running the joint web through a pair of rollers with cutting tools, and the attachment of the first web to the second web may be done by letting the joint web pass through a pair of rollers equipped with, for instance, welding tools, gluing tools, needling tools, ultrasound tools or laser tools.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A process for manufacturing of an absorbent article, said process comprising:
continuously feeding a first web along a travelling path, said first web having a longitudinal direction coinciding with said travelling path and a transverse direction perpendicular to said longitudinal direction, said first web comprising a first strip and a second opposing strip extending in the longitudinal direction and a first panel portion located therebetween,
continuously feeding a second web along a travelling path, said second web having a longitudinal direction coinciding with said travelling path and a transverse direction perpendicular to said longitudinal direction, said second web comprising a third strip and a fourth opposing strip and a second panel portion located therebetween, cutting the first panel portion into a number of first panels, which first panels are attached to the first and second strips, cutting the second panel portion into a number of second panels, which second panels are attached to the third and fourth strips, forming a joint web by placing the second web over the first web and attaching the first web to the second web along attachment lines such that the panels and the strips along the attachment lines divide the joint web into a number of absorbent articles, and cutting the joint web along the attachment lines thereby forming the absorbent articles.

2. The process according to claim 1, wherein the process further comprises:

cutting the first panel portion along generally transversely extending first and second cutting lines in such a way that the first panel portion is separated into a number of first front panels comprising a first forward part attached to the second strip and an opposing first central part attached to the first strip, and a number of first back panels comprising a first rear part attached to the first strip and an opposing second central part attached to the second strip, cutting the second panel portion along generally transversely extending third and fourth cutting lines in such a way that the second panel portion is separated into a number of second front panels comprising a second forward part attached to the fourth strip and an opposing third central part attached to the third strip, and a number of second back panels comprising a second rear part attached to the third strip and an opposing fourth central part attached to the fourth strip, bringing together the first web and the second web thereby forming a continuously fed joint web such that the first front panels are placed against the second back panels with the first central parts against the fourth central parts, and the second front panels are placed against the first back panels with the second central parts against the third central parts, attaching the second central parts to the third central parts by first seams along first attachment lines coinciding at least partly with the second and third strips, and attaching the first central parts to the fourth central parts by second seams along second attachment lines coinciding at least partly with the first and fourth strips, thereby forming the central portions of the absorbent articles, and cutting the joint web such that parts of the first and fourth strips together with the first back panel and the second front panel form an absorbent article separated from the joint web, and such that parts of the second and third strips together with the second back panel and the first front panel form an absorbent article separated from the joint web.

3. The process according to claim 2, wherein the first web is cut in such a way that each first and second front panel obtains a two-dimensional funnel shape, and each first and second back panel obtains a two-dimensional cup shape.

4. The process according to claim 1, wherein the first front and back panels are cut in such a way that they appear in an alternating pattern on the first web, and that the second front and back panels are cut in such a way that they appear in an alternating pattern on the second web.

5. The process according to claim 4, wherein the cutting is done in such a way that the first front and back panels are aligned in said longitudinal direction of said first web with every first front panel being rotated 180° with respect to every first back panel.

6. The process according to claim 4, wherein the cutting is done in such a way that the second front and back panels are aligned in said longitudinal direction of said second web with every second front panel being rotated 180° with respect to every second back panel.

7. The process according to claim 1, wherein the attaching the first web to the second web along the attachment lines in the forming of the joint web comprises:

attaching the first strip to the fourth strip by third seams at the attachment lines and attaching the second strip to the third strip by fourth seams at the attachment lines, thereby forming side portions of the absorbent article.

8. The process according to claim 7, wherein the process of forming an absorbent article separated from the joint web further comprises:

cutting the joint web along a fifth cutting line between the third seams and also along first attachment lines and cutting the joint web along a sixth cutting line between the fourth seams and also along second attachment lines, such that the cutting lines form connected cutting lines, severing individual absorbent articles from the joint web.

9. The process according to claim 1, wherein the process further comprises:

placing first absorbent bodies along the first web with a predetermined distance between the absorbent bodies.

10. The process according to claim 9, wherein the first absorbent bodies are applied to the first web in a double folded manner.

11. The process according to claim 9, wherein the first absorbent bodies are applied to the first web, and that;

second absorbent bodies are applied to the second web at a predetermined distance between the absorbent bodies.

12. The process according to claim 1, wherein that the process further comprises:

applying elastic means to the first web and/or to the second web.

* * * * *